US007153666B2

(12) United States Patent
Yuan et al.

(10) Patent No.: US 7,153,666 B2
(45) Date of Patent: Dec. 26, 2006

(54) METHODS AND COMPOSITIONS FOR DETERMINATION OF GLYCATED PROTEINS

(75) Inventors: Chong-Sheng Yuan, San Diego, CA (US); Abhijit Datta, Carlsbad, CA (US); Yuping Wang, San Diego, CA (US)

(73) Assignee: General Atomics, San Diego, CA (US)

( * ) Notice: Subject to any disclaimer, the term of this patent is extended or adjusted under 35 U.S.C. 154(b) by 145 days.

(21) Appl. No.: 10/622,893

(22) Filed: Jul. 17, 2003

(65) Prior Publication Data

US 2005/0014935 A1    Jan. 20, 2005

(51) Int. Cl.
   C12Q 1/37    (2006.01)
   C12Q 1/26    (2006.01)
   C12Q 1/28    (2006.01)
   C12Q 1/54    (2006.01)
   C12N 9/02    (2006.01)

(52) U.S. Cl. .......................... 435/23; 435/189; 435/25; 435/28; 435/14; 435/24; 530/350; 530/387.3; 530/387.9; 536/23.2; 536/23.4; 424/94.4

(58) Field of Classification Search ............ 435/189; 530/350, 387.3, 387.9; 424/94.4; 536/23.2, 536/23.4
See application file for complete search history.

(56) References Cited

U.S. PATENT DOCUMENTS

| | | |
|---|---|---|
| 2,713,581 A | 7/1955 | Pannone and Rust |
| 4,588,684 A | 5/1986 | Brake ......................... 435/68 |
| 4,837,331 A | 6/1989 | Yamanishi et al. |
| 4,847,195 A | 7/1989 | Khanna et al. ................. 435/7 |
| 4,948,729 A | 8/1990 | Piatak, Jr. et al. ............ 435/68 |
| 5,030,563 A | 7/1991 | Schendel et al. ........... 435/698 |
| 5,137,821 A | 8/1992 | Sagai et al. ................. 435/190 |
| 5,171,670 A | 12/1992 | Kronenberg et al. ....... 435/68.1 |
| 5,196,314 A | 3/1993 | Town et al. |
| 5,229,286 A | 7/1993 | Jarsch et al. ................ 435/190 |
| 5,244,796 A | 9/1993 | Levy et al. .................. 435/190 |
| 5,308,770 A | 5/1994 | Jarsch et al. ................ 435/190 |
| 5,312,759 A | 5/1994 | Hama et al. |
| 5,344,770 A | 9/1994 | Hitomi et al. ............. 435/71.2 |
| 5,681,529 A | 10/1997 | Taguchi et al. |
| 5,710,248 A | 1/1998 | Grose ......................... 530/327 |
| 5,712,138 A | 1/1998 | Kato et al. .................. 435/190 |
| 5,789,221 A | 8/1998 | Kato et al. .................. 435/190 |
| 5,824,527 A | 10/1998 | Kato et al. .................. 435/191 |
| 5,856,104 A | 1/1999 | Chee et al. ..................... 435/6 |
| 5,879,921 A | 3/1999 | Cherry et al. ............... 435/190 |
| 5,885,811 A | 3/1999 | Hansen ..................... 435/172.3 |
| 5,914,250 A | 6/1999 | Hansen ...................... 435/69.1 |
| 5,948,659 A | 9/1999 | Kato et al. .................. 435/189 |
| 5,948,665 A | 9/1999 | Matsukawa et al. ........ 435/194 |
| 5,972,294 A | 10/1999 | Smith et al. |
| 5,972,671 A | 10/1999 | Kato et al. .................. 435/191 |
| 5,985,591 A | 11/1999 | Yonehara et al. ............. 435/28 |
| 6,008,006 A | 12/1999 | Torrens et al. ................ 435/23 |
| 6,069,297 A | 5/2000 | Luzzatto et al. .............. 800/18 |
| 6,127,138 A | 10/2000 | Ishimaru et al. .............. 435/23 |
| 6,127,345 A | 10/2000 | Burnham ..................... 514/44 |
| 6,194,200 B1 | 2/2001 | Rose et al. ............. 435/320.1 |
| 6,352,835 B1 | 3/2002 | Komori et al. |
| 6,514,720 B1 | 2/2003 | Komori et al. |

FOREIGN PATENT DOCUMENTS

| | | |
|---|---|---|
| EP | 0 121 352 | 10/1984 |
| EP | 0 186 643 | 7/1986 |
| EP | 0 196 864 | 10/1986 |
| EP | 0 196864 | 10/1986 |
| EP | 0 239 931 | 3/1987 |
| EP | 0 821 064 | 1/1998 |
| EP | 1 223 224 | 7/2002 |
| GB | 738585 | 10/1955 |
| GB | 1 513 488 | 6/1978 |
| WO | WO 89/03886 | 5/1989 |
| WO | WO-90/12113 | 10/1990 |
| WO | WO 93/06125 | 4/1993 |
| WO | WO 96/28556 | 9/1996 |
| WO | WO 01/47968 | 12/1999 |
| WO | WO 01/68694 | 3/2000 |
| WO | WO 00/28041 | 5/2000 |
| WO | WO 01/90325 | 11/2001 |
| WO | WO 01/90378 | 11/2001 |
| WO | WO 01/98472 | 12/2001 |
| WO | WO 02/20795 | 3/2002 |
| WO | WO 02/064760 | 8/2002 |
| WO | WO 02/072634 | 9/2002 |
| WO | WO 03/042389 | 5/2003 |

OTHER PUBLICATIONS

Allgrove and Cockrill, Archives of Disease in Childhood, 63:418-422 (1988).
Armbuster, Fructosamine: Clin. Chem., 33(12):2153-63 (1987).
Baker et al., Clin. Chem., 37(4):552-556 (1991).

(Continued)

*Primary Examiner*—Rebecca E. Prouty
*Assistant Examiner*—Malgorzata A. Walicka
(74) *Attorney, Agent, or Firm*—Morrison & Foerster LLP

(57) ABSTRACT

This invention relates generally to the field of glycated protein detection. In particular, the invention provides chimeric proteins, nucleic acids encoding the chimeric proteins, methods and kits for assaying for a glycated protein in a sample, using inter alia, an amadoriase.

35 Claims, 5 Drawing Sheets

OTHER PUBLICATIONS

Bastin et al., Mol. Biochem. Parasitology, 77:235-239 (1996).
Baynes and Monnier (eds.), Prog. Clin. Biol. Res., 304:1-410 (1989).
Biochemistry 11(9): 1726-32 (1972).
Chen and Katz, BioTechniques, 25(1):22-24 (1998).
Diazyme Laboratories Division, General Atomics, FAOX-TE fact sheet, 5 pages.
Fossati et al., Clin. Chem. 26(2):227-231 (1980).
Frederick et al., J. Biol. Chem., 265(7):3793-802 (1990).
Gerhardinger et al., J. Biol. Chem., 270(1):218-224 (1995).
Hardy and Randall, J. Cell Sci. Suppl., 11:29-43 (1989).
Hobom et al., Dev. Biol. Stand., 84:255-262 (1995).
Kouzuma et al. Clin. Chimi. Acta, 324:61-71 (2002).
Kuhn et al., Mol. Gen. Genet., 167(3):235-241 (1979).
Michiels et al., Trends Microbiol., 9(4):164-168 (2001).
Nagelkerken et al., Electrophoresis, 18:2694-98 (1997).
Olah et al., Biochem., 221:94-102 (1994).
Peakman et al., Nucleic Acids Res., 20(22):6111-12 (1992).
Phillipou et al., Clin. Chem. 34(8):1561-64 (1988).
Prickett et al., BioTechniques, 7(6):580-584 (1989).
Roesser and Yanofsky, Nucleic Acids Res., 19(4):795-800 (1991).
Rudiger et al., Biotechniques, 23(1):96-97 (1997).
Saier et al., FASEB J., 2(3):199-208 (1988).
Sakai et al., Biosci. Biotech. Biochem., 59(3):487-491 (1995).
Schleicher et al., Clin. Chem. 34(2):320-323 (1988).
Sigma-Aldrich Catalog No. 82452, 1 page, printed Mar. 2, 2004.
Takahashi et al., J. Biol. Chem., 272(19):12505-7 (1997).
Takahashi et al., J. Biol. Chem., 272(6):3437-43 (1997).
Tolbert and Lameh, J. Neurochem., 70:113-119 (1998).
Tseng and Verma, Gene, 169:287-288 (1996).
Wang et al., Gene, 169(1):53-58 (1996).
Watson et al., Molecular Biology of the Gene, 4th Ed., 1987, The Bejacmin/Cummings Pub. Co., p. 224.
Worthington Catalog, Proteinase K, http://worthington-biochem.com/⎯/PROK.html., printed Mar. 2, 2004, 4 pages.
Xie et al., Endocrinology, 139(11):4563-67 (1998).
Gerhardinger et al., The Journal of Biological Chemistry (1995) 270(1):218-224.
International Search Report for PCT/US2004/022908, mailed on Jan. 26, 2005, 5 pages.
Invitrogen Catalogue, "pBAD TOPO TA Expression Kit," (2002) p. 75.
Yoshida et al., Applied and Environmental Microbiology (1995) 61(12):4487-4489.
Yoshida et al., European Journal of Biochemistry (1996) 242(3):499-505.

METHODS AND COMPOSITIONS FOR DETERMINATION OF GLYCATED PROTEINS

BACKGROUND OF THE INVENTION

A glycated protein is a substance which is produced by the non-enzymatic and irreversible binding of the amino group of an amino acid constituting a protein, with the aldehyde group of a reducing sugar such as aldose. See e.g., U.S. Pat. No. 6,127,138. Such a non-enzymatic and irreversible binding reaction is also called "Amadori rearrangement," and therefore the above-mentioned glycated protein may also be called "Amadori compound" in some cases.

Nonenzymatic glycation of proteins has been implicated in the development of certain diseases, e.g., diabetic complications and the aging process (Takahashi et al., *J. Biol. Chem.*, 272(19):12505–7 (1997); and Baynes and Monnier, *Prog. Clin. Biol. Res.*, 304:1–410 (1989)). This reaction leads to dysfunction of target molecules through formation of sugar adducts and cross-links. Considerable interest has focused on the Amadori product that is the most important "early" modification during nonenzymatic glycation in vitro and in vivo.

Various assays for glycated proteins are known. For example, U.S. Pat. No. 6,127,138 discloses that a sample containing a glycated protein is treated with Protease XIV or a protease from *Aspergillus* genus, thereafter (or while treating the sample with the above protease) FAOD (fructosyl amino acid oxidase) is caused to react with the sample so as to measure the amount of oxygen consumed by the FAOD reaction or the amount of the resultant reaction product, thereby to measure the glycated protein.

In another example, U.S. Pat. No. 6,008,006 discloses that the amount of glycated proteins in a sample can be quantified by reacting the sample with first a reagent which is a combination of a protease and a peroxidase and second with a ketoamine oxidase. U.S. Pat. No. 6,008,006 also discloses a kit which contains the combined peroxidase/protease enzyme reagent and also the ketoamine oxidase.

BRIEF SUMMARY OF THE INVENTION

In one aspect, the present invention is directed to an isolated chimeric protein, which chimeric protein comprises, from N-terminus to C-terminus: a) a first peptidyl fragment comprising a bacterial leader sequence from about 5 to about 30 amino acid residues; and b) a second peptidyl fragment comprising an amadoriase.

In another aspect, the present invention is directed to an isolated nucleic acid comprising a nucleotide sequence encoding a chimeric protein, which chimeric protein comprises, from N-terminus to C-terminus: a) a first peptidyl fragment comprising a bacterial leader sequence from about 5 to about 30 amino acid residues; and b) a second peptidyl fragment comprising an amadoriase. Recombinant cells comprising the nucleic acid and methods for producing the chimeric protein using the nucleic acid are also provided.

In still another aspect, the present invention is directed to a method for assaying for a glycated protein in a sample, which method comprises: a) contacting a sample to be assayed with a protease to generate a glycated peptide or a glycated amino acid from a glycated protein, if contained in said sample; b) contacting said generated glycated peptide or glycated amino acid with a chimeric protein comprising, from N-terminus to C-terminus: i) a first peptidyl fragment comprising a bacterial leader sequence from about 5 to about 30 amino acid residues; and ii) a second peptidyl fragment comprising an amadoriase, to oxidize said glycated peptide or glycated amino acid; and c) assessing oxidation of said glycated peptide or glycated amino acid by said chimeric protein to determine the presence and/or amount of said glycated protein in said sample.

In yet another aspect, the present invention is directed to a kit for assaying for a glycated protein in a sample, which kit comprises: a) a protease to generate glycated peptide or glycated amino acid from a glycated protein, if contained in a sample; b) the above-described chimeric protein to oxidize said glycated peptide or glycated amino acid; and c) means for assessing oxidation of said glycated peptide or glycated amino acid by said chimeric protein to determine the presence and/or amount of said glycated protein in said sample.

In yet another aspect, the present invention is directed to a method for assaying for a glycated protein in a sample, which method comprises: a) contacting a sample to be assayed with a proteinase K to generate a glycated peptide or a glycated amino acid from a glycated protein, if contained in said sample; b) contacting said generated glycated peptide or glycated amino acid with an amadoriase to oxidize said glycated peptide or glycated amino acid; and c) assessing oxidation of said glycated peptide or glycated amino acid by said amadoriase to determine the presence and/or amount of said glycated protein in said sample.

In yet another aspect, the present invention is directed to a kit for assaying for a glycated protein in a sample, which kit comprises: a) a proteinase K to generate a glycated peptide or a glycated amino acid from a glycated protein, if contained in said sample; b) an amadoriase to oxidize said glycated peptide or glycated amino acid; and c) means for assessing oxidation of said glycated peptide or glycated amino acid by said amadoriase to determine the presence and/or amount of said glycated protein in said sample.

BRIEF DESCRIPTION OF THE SEVERAL VIEWS OF THE DRAWING(S)

DETAILED DESCRIPTION OF THE INVENTION

Figure 1:
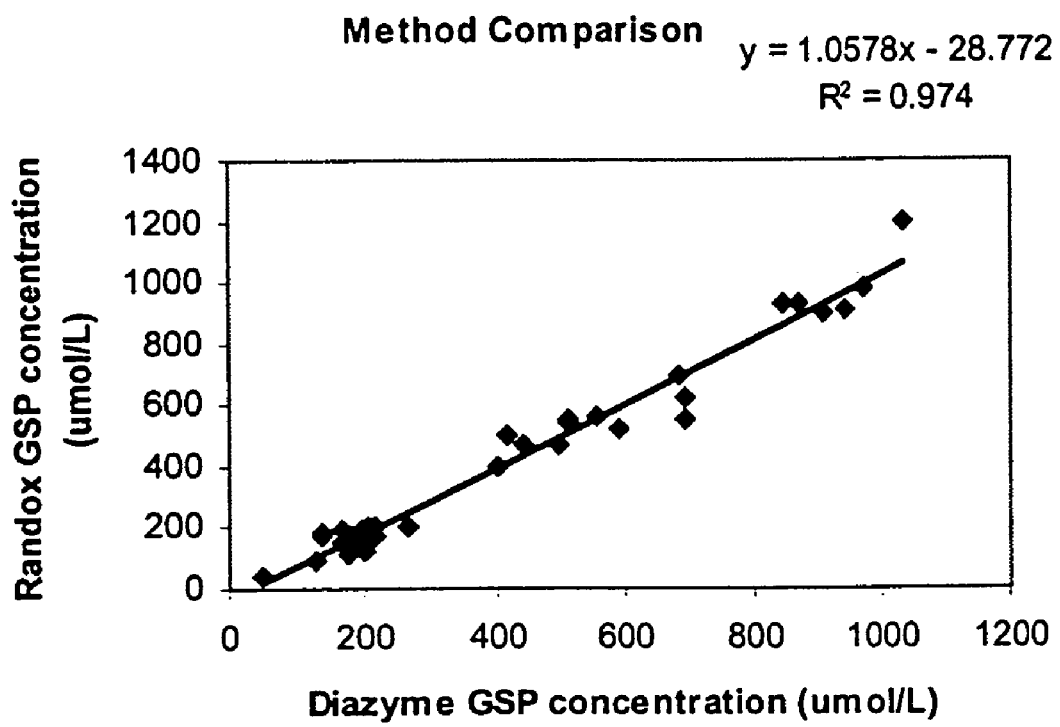
FIG. 1 illustrates a comparison between an exemplary GSP (glycated serum protein) kit and a Randox Fructosamine kit.

For clarity of disclosure, and not by way of limitation, the detailed description of the invention is divided into the subsections that follow.

A. Definitions

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, a "leader sequence" refers to a peptide sequence, when fused to a target peptide or protein, increases stability and/or expression level of the target peptide or protein. Normally, a leader sequence increases stability and/or expression level of the target peptide or protein for at least 50%. Preferably, a leader sequence increases stability and/or expression level of the target peptide or protein for at least 1 fold, 2 folds, 5 folds, 10 folds or more than 10 folds. In the regulation of gene expression for enzymes concerned with amino acid synthesis in prokaryotes, the leader sequence codes for the leader peptide that contains several residues of the amino acid being regulated. Transcription is closely linked to translation, and if translation is retarded by limited supply of aminoacyl tRNA for the specific amino acid, the mode of transcription of the leader sequence permits full transcription of the operon genes; otherwise complete transcription of the leader sequence prematurely terminates transcription of the regulated gene.

As used herein, a "glycated protein" refers to a substance which is produced by the non-enzymatic and irreversible binding of the amino group of an amino acid constituting a protein, with the aldehyde group of a reducing sugar such as aldose. See e.g., U.S. Pat. No. 6,127,138. Such a non-enzymatic and irreversible binding reaction is also called "Amadori rearrangement," and therefore the above-mentioned glycated protein may also be called "Amadori compound" in some cases.

As used herein, an "amadoriase" refers to an enzyme catalyzing the oxidative deglycation of Amadori products to yield corresponding amino acids, glucosone, and $H_2O_2$, as shown in the following reaction:

$$R_1-CO-CH_2-NH-R_2+O_2+H_2O \rightarrow R_1-CO-CHO+R_2-NH_2+H_2O_2$$

wherein, $R_1$ represents the aldose residue of a reducing sugar and $R_2$ represents a residue of an amino acid, protein or peptide. Other synonyms of amadoriase include fructosyl amino acid oxidase (FAOD) and fructosyl amine:oxygen oxidoreductase (FAOO). For purposes herein, the name "amadoriase" is used herein, although all such chemical synonyms are contemplated. "Amadoriase" also encompasses a functional fragment or a derivative that still substantially retain its enzymatic activity catalyzing the oxidative deglycation of Amadori products to yield corresponding amino acids, glucosone, and $H_2O_2$. Typically, a functional fragment or derivative retains at least 50% of its amadoriase activity. Preferably, a functional fragment or derivative retains at least 60%, 70%, 80%, 90%, 95%, 99% or 100% of its amadoriase activity. It is also intended that an amadoriase can include conservative amino acid substitutions that do not substantially alter its activity. Suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson, et al., *Molecular Biology of the Gene*, 4th Edition, 1987, The Bejacmin/Cummings Pub. Co., p. 224). Such exemplary substitutions are preferably made in accordance with those set forth in TABLE 1 as follows:

TABLE 1

| Original residue | Conservative substitution |
|---|---|
| Ala (A) | Gly; Ser |
| Arg (R) | Lys |
| Asn (N) | Gln; His |
| Cys (C) | Ser |
| Gln (Q) | Asn |
| Glu (E) | Asp |
| Gly (G) | Ala; Pro |
| His (H) | Asn; Gln |
| Ile (I) | Leu; Val |
| Leu (L) | Ile; Val |
| Lys (K) | Arg; Gln; Glu |
| Met (M) | Leu; Tyr; Ile |
| Phe (F) | Met; Leu; Tyr |
| Ser (S) | Thr |
| Thr (T) | Ser |
| Trp (W) | Tyr |
| Tyr (Y) | Trp; Phe |
| Val (V) | Ile; Leu |

Other substitutions are also permissible and may be determined empirically or in accord with known conservative substitutions.

As used herein, "glycohemoglobin" refers to a fructosylamine derivative produced by the glycation of hemoglobin in blood.

As used herein, "glycoalbumin" refers to a fructosylamine derivative produced by the glycation of albumin in blood.

As used herein, "fructosamine" refers to a derivative (having a reducing ability) produced by the glycation of a protein in blood.

As used herein, a "composition" refers to any mixture of two or more products or compounds. It may be a solution, a suspension, liquid, powder, a paste, aqueous, non-aqueous, or any combination thereof.

As used herein, a "combination" refers to any association between two or among more items.

As used herein, "plasma" refers to the fluid, noncellular portion of the blood, distinguished from the serum obtained after coagulation.

As used herein, "serum" refers to the fluid portion of the blood obtained after removal of the fibrin clot and blood cells, distinguished from the plasma in circulating blood.

As used herein, "fluid" refers to any composition that can flow. Fluids thus encompass compositions that are in the form of semi-solids, pastes, solutions, aqueous mixtures, gels, lotions, creams, and other such compositions.

As used herein, "peroxidase" refers to an enzyme that catalyses a host of reactions in which hydrogen peroxide is a specific oxidizing agent and a wide range of substrates act as electron donors. It is intended to encompass a peroxidase with conservative amino acid substitutions that do not substantially alter its activity. The chief commercially available peroxidase is horseradish peroxidase.

As used herein, "glucose oxidase" refers to an enzyme that catalyzes the formation of gluconic acid and $H_2O_2$ from glucose, $H_2O$ and $O_2$. It is intended to encompass glucose oxidase with conservative amino acid substitutions that do not substantially alter its activity.

As used herein, "hexokinase" refers to an enzyme that catalyses the transfer of phosphate from ATP to glucose to form glucose-6-phosphate, the first reaction in the metabolism of glucose via the glycolytic pathway. It is intended to encompass hexokinase with conservative amino acid substitutions that do not substantially alter its activity.

As used herein, the abbreviations for any protective groups, amino acids and other compounds, are in accord with their common usage, recognized abbreviations, or the IUPAC-IUB Commission on Biochemical Nomenclature, unless otherwise indicated (see *Biochemistry* 11: 1726 (1972)).

B. Chimeric Proteins Comprising an Amadoriase and Nucleic Acids Encoding the Same In one aspect, the present invention is directed to an isolated chimeric protein, which chimeric protein comprises, from N-terminus to C-terminus: a) a first peptidyl fragment comprising a bacterial leader sequence from about 5 to about 30 amino acid residues; and b) a second peptidyl fragment comprising an amadoriase.

Any suitable bacterial leader sequences can be used. As disclosed in U.S. Pat. No. 6,194,200,expression of the polypeptide of interest as a fused protein with a leader sequence from another gene has several advantages in addition to providing for stability. For example, the presence of the N-terminal amino acids provides a means for using general purification techniques for purification of any of a variety of polypeptides. For example, the N-terminal amino acids of the N-protein are predictably antigenic, and thus specific antibodies raised against the N-terminal amino acids of the N-protein may be used for the amino purification of the fusion proteins containing the N-terminus of the N-protein. Furthermore, the N-terminus of the N-protein has a high positive charge, which facilitates purification of the desired protein by ion-exchange chromatography, and the like.

The leader sequence can also be a hydrophobic amino acid sequence, which may additionally function as a signal sequence for secretion. See U.S. Pat No. 6,194,200. A DNA sequence encoding the signal sequence is joined upstream from and in reading frame with the gene of interest. Typically, the signal sequence includes a cleavage site which is recognized by a signal sequence peptidase. Thus, positioning the polypeptide of interest directly after the signal sequence cleavage site will allow it to be specifically cleaved from the signal sequence and secreted as a mature polypeptide. Examples of hydrophobic amino acid sequences include the bacterial alkaline phosphatase signal sequence; the OMP-A, B, C, D, E or F signal sequences; the LPP signal sequence, β-lactamase signal sequence; and toxin signal sequences.

Other leader sequences which can be used include hydrophilic sequences, for example the N-terminal 41 amino acid residues from amphiregulin which may provide for modification of the function of the polypeptide of interest. See U.S. Pat. No. 6,194,200. In addition, a cytotoxic agent such as a toxin A-chain fragment, ricin A-chain, snake venom growth arresting peptide, or a targeting molecule such as a hormone or antibody can be coupled covalently with the leader sequence with in most cases minimal effect on the biological activity of the gene product of interest. As with the other leader sequences, a DNA sequence encoding the leader sequence is joined upstream from and in reading frame with the gene of interest.

Where the leader sequence is not a signal sequence or does not contain a convenient natural cleavage site, additional amino acids may be inserted between the gene of interest and the leader sequence to provide an enzymatic or chemical cleavage site for cleavage of the leader peptide, following purification of the fusion protein, to allow for subsequent purification of the mature polypeptide. See U.S. Pat. No. 6,194,200. For example, introduction of acid-labile aspartyl-proline linkages between the two segments of the fusion protein facilitates their separation at low pH. This method is not suitable if the desired polypeptide is acid-labile. The fusion protein may be cleaved with, for example, cyanogen bromide, which is specific for the carboxy side of methionine residues. Positioning a methionine between the leader sequence and the desired polypeptide would allow for release of the desired polypeptide. This method is not suitable when the desired polypeptide contains methionine residues.

Other bacterial leader sequences disclosed in the following patents, patent application and references can also be used: WO 00/28041 and WO 89/03886; U.S. Pat. Nos. 5,914,250, 5,885,811, 5,171,670, 5,030,563, 4,948,729 and 4,588,684; EP Patent Nos. EP 0,196,864, EP 0,186,643 and EP 0,121,352; Michiels et al., *Trends Microbiol.*, 9(4):164–8 (2001); Hobom et al., *Dev. Biol. Stand.*, 84:255–62 (1995); Hardy and Randall, *J. Cell. Sci. Suppl.*, 11:29–43 (1989); Saier et al., *FASEB J.*, 2(3 :199–208 (1988); and Peakman et al., *Nucleic Acids Res.*, 20(22):6111–2 (1992). Preferably, the bacterial leader sequence is a leader sequence of an *E.coli*. protein, e.g., the *E.coli*. leader sequences disclosed in Roesser and Yanofsky, *Nucleic Acids Res.*, 19(4 :795–800 (1991); and Kuhn et al., *Mol. Gen. Genet.*, 167(3):235–41 (1979).

In one example, the leader sequence has at least 40% identity to the amino acid sequence set forth in SEQ ID NO:1 (MGGSGDDDDLAL), in which the percentage identity is determined over an amino acid sequence of identical size to the amino acid sequence set forth in SEQ ID NO:1. Preferably, the leader sequence has at least 50%, 60%, 70%, 80%, 90%, 95%, 99% or 100% identity to the amino acid sequence set forth in SEQ ID NO:1, in which the percentage identity is determined over an amino acid sequence of identical size to the amino acid sequence set forth in SEQ ID NO:1. Also preferably, the leader sequence binds to an antibody that specifically binds to an amino acid sequence set forth in SEQ ID NO:1. Still preferably, the leader sequence comprises the amino acid sequence set forth in SEQ ID NO:1.

The first peptidyl fragment can have any suitable length. For example, the first peptidyl fragment comprises about 5, 6, 7, 8, 9, 10, 11, 12, 13, 14, 15, 16, 17, 18, 19, 20, 21, 22, 23, 24, 25, ,26, 27, 28, 29 or 30 amino acid residues. Preferably, the first peptidyl fragment comprises about 20 amino acid residues.

Any suitable amadoriase can be used. In one example, the amadoriase is of *Aspergillus* sp. origin (See e.g., Takahashi et al., *J. Biol. Chem.*, 272(6):3437–43 (1997)). In another example, the amadoriase uses FAD as a cofactor. Preferably, the amadoriase has a FAD cofactor-binding consensus sequence Gly-X-Gly-X-X-Gly (SEQ ID NO:2), X being any amino acid residue. In still another example, the amadoriase is amadoriase Ia, amadoriase Ib, amadoriase Ic or amadoriase II (See e.g., Takahashi et al., *J. Biol. Chem.*, 272(6 :3437–43 (1997)). Amino acid sequence homology between the N-terminal sequence of amadoriases Ia, amadoriase Ib, amadoriase Ic and amadoriase II is shown in the following Table 2. These data were obtained by a computerized search using the combined GenBank™ CDS translations/PDB/SwissProt/SPupdate/PIR data base (See Table IV of Takahashi et al., *J. Biol. Chem.*, 272(6):3437–43 (1997)). Numbers indicate the amino acid positions within each sequence. Conservative substitutions are indicated by (+). The data of amadoriases correspond to the N-terminal sequences obtained in Takahashi et al., *J. Biol. Chem.*, 272(6):3437–43 (1997).

TABLE 2

Amino acid sequence homology between
the N-terminal sequence of amadoriase Ia,
amadoriase Ib, amadoriase Ic and
amadoriase II

| Protein | Sequences with residue nos. | SEQ ID NO |
|---|---|---|
| Amadoriases Ia | $^1$APSILSTESSI (C/T)VIGAGTW G$^{20}$ | SEQ ID NO:7 |
| Amadoriase Ib | $^1$APSILSTESSII VIGAGTWG$^{20}$ | SEQ ID NO:8 |
| Amadoriase Ic | $^1$STESSIIVIGA GTWG(C)(S)TAL$^{20}$ | SEQ ID NO:9 |
| Amadoriase II | $^1$AVTKSSSLLI VGAGTWGTS T$^{20}$ | SEQ ID NO:10 |

Other amadoriases, e.g., amadoriases disclosed in GenBank Accession No. U82830 (Takahashi et al., *J. Biol. Chem.*, 272(19):12505–12507 (1997) and amadoriases disclosed U.S. Pat. No.6,127,138 can also be used. A functional fragment or a derivative of an amadoriase that still substantially retain its enzymatic activity catalyzing the oxidative deglycation of Amadori products to yield corresponding amino acids, glucosone, and $H_2O_2$ can also be used.

Normally, a functional fragment or a derivative of an amadoriase retain at least 50% of its enzymatic activity. Preferably, a functional fragment or a derivative of an amadoriase retain at least 50%, 60%, 70%, 80%, 90%, 95%, 99% or 100% of its enzymatic activity.

Assays for enzymatic activities of amadoriases are known in the art (See e.g., Takahashi et al., *J. Biol. Chem.*, 272(6): 3437–43 (1997) and U.S. Pat. No. 6,127,138). Four exemplary assays for enzymatic activities of amadoriases are disclosed in Takahashi et al., *J. Biol. Chem.*, 272(6):3437–43 (1997).

Glucosone Formation

In this assay, the enzyme activity is monitored by the release of glucosone measured by a colorimetric reaction with OPD using fructosyl propylamine as a substrate. This assay is based on the end point measurement of glucosone formed after 120 min of reaction time. The reaction mixture contains 20 mM sodium phosphate, pH 7.4, 10 mM OPD, 10 mM fructosyl propylamine, and enzyme protein in a final volume of 1 ml. After incubation at 37° C. for 2 h, the absorbance at 320 nm is measured. The reaction is linear to 240 min in a dose-dependent manner under these conditions. One unit of enzyme activity is defined as the amount of the enzyme that produces 1 μmol of glucosone/min. Synthesized glucosone is used as a standard.

Free Amine Assay

To assay the release of free amine, fluorescence is measured after reaction with fluorescamine. Twenty-five (25) μl of a solution of pure enzyme or enzyme-rich fraction, 15 μl of 20% fructosyl propylaminein water, and 250 μl of PBS are incubated at 37° C. for different times as indicated. The reaction is stopped by filtration through a Microcon-10 (Amicon, Beverly, Mass.) at 4 C. One (1) μl of the pure or 1:10 diluted filtrate is added to 1.5 ml of 50 MM phosphate buffer pH 8.0. Under vigorous vortexing 0.5 ml of 0.03% fluorescamine in dioxane is rapidly added. After 5 min fluorescence is measured ($\lambda_{ex}$=390 nm, $\lambda_{em}$=475 nm). A standard plot is made with 6–150 ng of propylamine.

$H_2O_2$ Assay

Hydrogen peroxide is quantitated by the quinone dye assay according to Sakai et al., *Biosci. Biotech. Biochem.*, 59:487–491 (1995). The reaction mixture contains 20 mM Tris-HCl, pH 8.0, 1.5 mM 4-aminoantipyrine, 2.0 mM phenol, 2.0 units of peroxidase, 10 mM fructosyl propylamine, and enzyme protein in a total volume of 1 ml. Production of the $H_2O_2$ is monitored by the formation of a quinone dye following the absorbance at 505 nm ($\epsilon$=5.13× $10^3$). The production of 0.5 μmol of quinone dye corresponds to the formation of 1.0 μmol of $H_2O_2$.

Oxygen Consumption

Oxygen consumption is determined with a YSI-Beckman glucometer II equipped with a Clarke type oxygen electrode as described in Gerhardinger, et al., *J. Biol. Chem.*, 270: 218–224 (1995). Briefly, enzyme (50 μl) is added to the chamber containing 750 μl of PBS and 650 μl of water. The reaction is started by addition of 50 μl of 300 mM fructosyl propylamine (final concentration 10 mM).

In another example, the amadoriase has at least 40% identity to the amino acid sequence set forth in SEQ ID NO:3 (AVTKSSSLLIVGAGTWGTSTALHLARR-GYTNVTVLDPYPVPSAISAGNDV NKVISSGQYSNN-KDEIEVNEILAEEAFNGWKNDPLFKPYY-HDTGLLMSAC SQEGLDRLGVRVRPGEDPNLVELTRPEQ-FRKLAPEGVLQGDFPGWKGYF ARSGAGWAHAR-NALVAAAREAQRMGVKFVTGTPQGRVVT-LIFENNDVK GAVTGDGKIWRAERTFLCAGASAGQFLD-FKNQLRPTAWTLVHIALKPEE RALYKNIPVIFNIERG-FFFEPDEERGEIKICDEHPGYTNMVQSADGTMMSIP FEKTQIPKEAETRVRALLKET-MPQLADRPFSFARICWCADTANREFLIDRH PQYH-SLVLGCGASGRGFKYLPSIGNLIV-DAMEGKVPQKIHELIKWNPDIAA NRNWRDTLGRFGGPNRVMDFHDVKEWT-NVQYRDISKL), in which the percentage identity is determined over an amino acid sequence of identical size to the amino acid sequence set forth in SEQ ID NO:3. Preferably, the amadoriase has at least 50%, 60%, 70%, 80%, 90%, 95%, 99% or 100% identity to the amino acid sequence set forth in SEQ ID NO:3, in which the percentage identity is determined over an amino acid sequence of identical size to the amino acid sequence set forth in SEQ ID NO:3. Also preferably, the amadoriase binds to an antibody that specifically binds to an amino acid sequence set forth in SEQ ID NO:3. Also preferably, the amadoriase comprises the amino acid sequence set forth in SEQ ID NO:3.

The first and second peptidyl fragments can be linked via any suitable linkage. For example, the first and second peptidyl fragments can be linked via a cleavable linkage.

The isolated chimeric protein can further comprise, at its C-terminus, a third peptidyl fragment comprising a second bacterial leader sequence from about 5 to about 30 amino acid residues. Any suitable bacterial leader sequences, including the ones described above, can be used.

In one example, the second bacterial leader sequence is a leader sequence of an *E. coli*. protein. in another example, the second bacterial leader sequence has at least 40% identity to the amino acid sequence set forth in SEQ ID NO:4 (KGELEGLPIPNPLLRTG), in which the percentage identity is determined over an amino acid sequence of identical size to the amino acid sequence set forth in SEQ ID NO:4. Preferably, the second bacterial leader sequence has at least 50%, 60%, 70%, 80%, 90%, 95%, 99% or 100% identity to the amino acid sequence set forth in SEQ ID NO:4, in which the percentage identity is determined over an amino acid sequence of identical size to the amino acid sequence set forth in SEQ ID NO:4. Also preferably, the second bacterial leader sequence binds to an antibody that specifically binds to an amino acid sequence set forth in SEQ ID NO:4. Also preferably, the second bacterial leader sequence comprises the amino acid sequence set forth in SEQ ID NO:4.

The third peptidyl fragment can have an suitable length. For example, the third peptidyl fragment comprises about 5, 6, 7, 8, 9, 10, 11, 12, 13, 14, 15, 16, 17, 18, 19, 20, 21, 22, 23, 24, 25, ,26, 27, 28, 29 or 30 amino acid residues. Preferably, the third peptidyl fragment comprises about 20 amino acid residues.

The isolated chimeric protein of can further comprise, at its C-terminus, a third peptidyl fragment comprising a peptide tag. Any suitable tag can be used. For example, the tag can be FLAG, HA, HA1, c-Myc, 6-His, AU1, EE, T7, 4A6, ε, B, gE and Ty1 tag (See Table 3).

-continued
RVVTLIFENNDVKGAVTGDGKIWRAERTFLCAGASAGQFLDFKNQLRPT

AWTLVHIALKPEERALYKNIPVIFNIERGFFFEPDEERGEIKICDEHPGY

TNMVQSADGTMMSIPFEKTQIPKEAETRVRALLKETMPQLADRPFSFARI

CWCADTANREFLIDRHPQYHSLVLGCGASGRGFKYLPSIGNLIVDAMEGK

VPQKIHELIKWNPDIAANRNWRDTLGRFGGPNRVMDFHDVKEWTNVQYRD

ISKLKGELEGLPIPNPLLRTGHHHHHH).

In another aspect, the present invention is directed to an isolated nucleic acid comprising a nucleotide sequence encoding a chimeric protein, which chimeric protein comprises, from N-terminus to C-terminus: a) a first peptidyl fragment comprising a bacterial leader sequence from about 5 to about 30 amino acid residues; and b) a second peptidyl fragment comprising an amadoriase.

In one example, the isolated nucleic acid comprises a nucleotide sequence encoding the chimeric protein comprising the amino acid sequence set forth in SEQ ID NO:5. In another example, the isolated nucleic acid comprises a nucleotide sequence set forth in SEQ ID NO:6

TABLE 3

Exemplary epitope tag systems

| Epitope | Peptide | SEQ ID | Antibody | Reference |
|---|---|---|---|---|
| FLAG | AspTyrLysAspAspAspLys | 11 | 4E11 | Prickett[1] |
| HA | TyrProTyrAspValPRoAspTyrAla | 12 | 12Ca5 | Xie[2] |
| HA1 | CysGlnAspLeuProGlyAsnAspAsnSerThr | 13 | mouse MAb | Nagelkerken[3] |
| c-Myc | GluGlnLysLeuIleSerGluGluAspLeu | 14 | 9E10 | Xie[2] |
| 6-His | HisHisHisHisHisHis | 15 | BAbCO* | |
| AU1 | AspThrTyrArgTyrIle | 16 | BAbCO | |
| EE | GluTyrMetProMetGlu | 17 | anti-EE | Tolbert[4] |
| T7 | AlaSerMetThrGlyGlyGlnGlnMetGlyArg | 18 | Invitrogen | Chen[5] Tseng[6] |
| 4A6 | SerPheProGlnPheLysProGlnGluIle | 19 | 4A6 | Rudiger[7] |
| ε | LysGlyPheSerTyrPheGlyGluAspLeuMetPro | 20 | anti-PKCε | Olah[8] |
| B | GlnTyrProAlaLeuThr | 21 | D11, F10 | Wang[9] |
| gE | GlnArgGlnTyrGlyAspValPheLysGlyAsp | 22 | 3B3 | Grose[10] |
| Ty1 | GluValHisThrAsnGlnAspProLeuAsp | 23 | BB2, TYG5 | Bastin[11] |

[1]Prickett, et al., BioTechniques, 7(6): 580–584 (1989)
[2]Xie, et al., Endocrinology, 139(11): 4563–4567 (1998)
[3]Nagelkerke, et al., Electrophoresis, 18: 2694–2698 (1997)
[4]Tolbert and Lameh, J. Neurochem., 70: 113–119 (1998)
[5]Chen and Katz, BioTechniques, 25(1): 22–24 (1998)
[6]Tseng and Verma, Gene, 169: 287–288 (1996)
[7]Rudiger, et al., BioTechniques, 23(1): 96–97 (1997)
[8]Olah, et al., Biochem., 221: 94–102 (1994)
[9]Wang, et al., Gene, 169(1): 53–58 (1996)
[10]Grose, U.S. Pat. No. 5,710,248
[11]Bastin, et al., Mol. Biochem. Parasitology, 77: 235–239 (1996) Invitrogen, Sigma, Santa Cruz Biotech In an example, the isolated chimeric protein comprises the amino acid sequence set forth in SEQ ID NO:5

(MGGSGDDDDLALAVTKSSSLLIVGAGTWGTSTALHLARRGYTNVTVLD

PYPVPSAISAGNDVNKVISSGQYSNNKDEIEVNEILAEEAFNGWKNDPLF

KPYYHDTGLLMSACSQEGLDRLGVRVRPGEDPNLVELTRPEQFRKLAPEG

VLQGDFPGWKGYFARSGAGWAHARNALVAAAREAQRMGVKFVTGTPQG (ATGGGAGGTTCGGGTGACGATGATGACCTGGCTCTCGCCGTCACTAA

GTCATCATCTCTCCTGATCGTTGGTGCCGGGACTTGGGGCACCTCAAC

GGCTCTGCACCTCGCGCGCCGCGGATATACCAACGTTACCGTGCTGGA

CCCCTATCCTGTCCCTAGCGCCATCTCCGCCGGAAACGACGTGAACAA

AGTCATTAGCAGTGGCCAATATTCGAATAACAAAGACGAAATCGAAG

```
                      -continued
TGAATGAGATCTTGGCGGAAGAGGCGTTTAACGGTTGGAAGAACGAC

CCGCTTTTCAAACCGTATTATCATGATACGGGCCTGCTGATGTCTGCTT

GCTCGCAGGAGGGCCTGGATCGCCTGGGCGTCCGGGTACGTCCGGGCG

AGGATCCTAATCTGGTGGAACTTACCCGCCCGGAGCAATTTCGTAAAC

TGGCCCCGGAAGGCGTGTTGCAAGGTGATTTTCCGGGTTGGAAAGGGT

ACTTTGCGCGTTCCGGCGCTGGCTGGGCACATGCAAGGAATGCCTTAG

TGGCAGCAGCACGCGAAGCACAGCGCATGGGTGTAAAATTTGTTACTG

GCACCCCGCAGGGTCGTGTAGTCACGTTAATCTTTGAAAATAACGATG

TAAAAGGTGCCGTTACGGGCGATGGCAAAATTTGGAGAGCGGAACGT

ACATTCCTGTGTGCTGGGGCTAGCGCGGGTCAGTTCCTAGATTTCAAG

AATCAACTTCGACCAACCGCTTGGACCCTGGTACACATTGCGTTAAAA

CCGGAAGAACGTGCGTTGTACAAAAATATACCGGTTATCTTTAACATC

GAACGGGGTTTTTCTTTGAACCCGATGAGGAGCGCGGTGAGATTAAA

ATATGCGATGAACACCCGGGCTACACAAATATGGTCCAGAGTGCAGA

CGGCACGATGATGAGCATTCCGTTCGAAAAAACCCAGATTCCAAAG

AAGCCGAAACGCGCGTTCGGGCCCTGCTGAAAGAGACAATGCCCCAG

CTGGCAGACCGTCCATTCAGCTTCGCACGCATTTGCTGGTGTGCCGAT

ACCGCGAATCGCGAATTCCTGATAGATCGACATCCGCAGTACCACAGT

CTTGTGTTGGGCTGTGGTGCGAGCGGAAGAGGGTTTAAATATCTGCCT

TCTATTGGGAATCTCATTGTTGACGCGATGGAAGGTAAAGTGCCGCAA

AAAATTCACGAATTAATCAAGTGGAACCCGGACATTGCGGCGAACCGT

AACTGGCGTGATACTCTGGGGCGTTTTGGCGGTCCAAATCGTGTGATG

GATTTTCATGATGTGAAGGAATGGACCAATGTTCAGTATCGTGATATT

TCCAAGCTGAAAGGAGAGTTGGAAGGTaaGCCAATCCCTAACCCGTTA

CTGCGCACAGGCCATCACCATCATCATCATTAA).
```

In still another example, the isolated nucleic acid comprising a nucleotide sequence complementary to the nucleotide sequence encoding a chimeric protein, which chimeric protein comprises, from N-terminus to C-terminus: a) a first peptidyl fragment comprising a bacterial leader sequence from about 5 to about 30 amino acid residues; and b) a second peptidyl fragment comprising an amadoriase.

A recombinant cell containing the nucleic acid, or a complementary strand thereof, encoding a chimeric protein, which chimeric protein comprises, from N-terminus to C-terminus: a) a first peptidyl fragment comprising a bacterial leader sequence from about 5 to about 30 amino acid residues; and b) a second peptidyl fragment comprising an amadoriase, is contemplated.

A method of producing a chimeric protein is also contemplated, which method comprising growing a recombinant cell containing the nucleic acid encoding a chimeric protein, which chimeric protein comprises, from N-terminus to C-terminus: a) a first peptidyl fragment comprising a bacterial leader sequence from about 5 to about 30 amino acid residues; and b) a second peptidyl fragment comprising an amadoriase, such that the encoded chimeric protein is expressed by the cell, and recovering the expressed chimeric protein. The product of the method is further contemplated.

The chimeric proteins and the nucleic acids encoding the chimeric proteins can be prepared by any suitable methods, e.g., chemical synthesis, recombinant production or a combination thereof (See e.g., Current Protocols in Molecular Biology, Ausubel, et al. eds., John Wiley & Sons, Inc. (2000) and Sambrook, et al., Molecular Cloning: A Laboratory Manual, Cold Spring Harbor Laboratory press, (1989)).

C. Methods and Kits for Assaying for a Glycated Protein using a Chimeric Protein In still another aspect, the present invention is directed to a method for assaying for a glycated protein in a sample, which method comprises: a) contacting a sample to be assayed with a protease to generate a glycated peptide or a glycated amino acid from a glycated protein, if contained in said sample; b) contacting said generated glycated peptide or glycated amino acid with a chimeric protein comprising, from N-terminus to C-terminus: i) a first peptidyl fragment comprising a bacterial leader sequence from about 5 to about 30 amino acid residues; and ii) a second peptidyl fragment comprising an amadoriase, to oxidize said glycated peptide or glycated amino acid; and c) assessing oxidation of said glycated peptide or glycated amino acid by said chimeric protein to determine the presence and/or amount of said glycated protein in said sample.

The present methods can be used to assay any suitable sample. Preferably, the sample is a blood sample, e.g., a plasma, serum, red blood cell or whole blood sample.

The present methods can be used to assay any suitable glycated proteins. Preferably, the glycated protein to be assayed is glycoalbumin or glycohemoglobin.

Any suitable protease can be used in the present methods. Either an endo-type protease or an exo-type protease can be used. Exemplary endo-type proteases include trypsin, α-chymotrypsin, subtilisin, proteinase K, papain, cathepsin B, pepsin, thermolysin, protease XVII, protease XXI, lysylendopeptidase, prolether and bromelain F. Exemplary exo-type proteases include an aminopeptidase or a carboxypeptidase. In one example, the protease is proteinase K, pronase E, ananine, thermolysin, subtilisin or cow pancreas proteases.

The protease can be used to generates a glycated peptide of any suitable size. For example, the protease can be used to generates a glycated peptide from about 2 to about 30 amino acid residues. In another example, the protease is used to generate glycated glycine, glycated valine or glycated lysine residue or a glycated peptide comprising glycated glycine, glycated valine or glycated lysine residue.

Any suitable chimeric proteins, including the ones described in the above Section B, can be used in the present methods. In one example, the chimeric protein comprises the amino acid sequence set forth in SEQ ID NO:5. In another example, the chimeric protein is encoded by the nucleotide sequence set forth in SEQ ID NO:6.

The oxidation of the glycated peptide or glycated amino acid can be assessed by any suitable methods. For example, the oxidation of the glycated peptide or glycated amino acid can be assessed by assessing consumption of the glycated peptide or glycated amino acid, $H_2O$ or $O_2$ in the oxidation reaction or the formation of the oxidized glucose (glucosone), $H_2O_2$ or the amino acid in the oxidation reaction.

The $O_2$ consumption by can be assessed by any suitable methods. For example, the $O_2$ consumption can be assessed by an oxygen electrode.

The $H_2O_2$ formation can be assessed by any suitable methods. For example, the $H_2O_2$ formation can be assessed by a peroxidase. Any peroxidase can be used in the present methods. More preferably, a horseradish peroxidase is used. For example, the horseradish peroxidases with the following GenBank accession Nos. can be used: E01651; D90116 (prxC3 gene); D90115 (prxC2 gene); J05552 (Synthetic isoenzyme C(HRP—C)); S14268 (neutral); OPRHC (C1 precursor); S00627 (C1C precursor); JH0150 (C3 precursor); S00626 (C1B precursor); JH0149 (C2 precursor); CAA00083 (Armoracia rusticana); and AAA72223 (synthetic horseradish peroxidase isoenzyme C (HRP—C)). In another example, the $H_2O_2$ formation can be assessed by a peroxidase and Trinder reaction. The glycated peptide or glycated amino acid can be contacted with the chimeric protein and the peroxidase sequentially or simultaneously.

The glucosone formation can be assessed by any suitable methods. For example, the glucosone formation can be assessed by a glucose oxidase. Any suitable glucose oxidase can be used. For example, glucose oxidases encoded by the nucleotide sequences with the following GenBank accession Nos. can be used: AF012277 (*Penicillium* amagasakiense); U56240 (*Talaromyces* flavus); X16061 (*Aspergillus niger* gox gene); X56443 (*A.niger* god gene); J05242 (*A.niger*); AF012277 (*Penicillium* amagasakiense); U56240 (*Talaromyces flavus*); X16061 (*Aspergillus niger* gox gene); X56443 (*A.niger* god gene); J05242 (*A.niger* glucose). Preferably, the nucleotide sequences with the GenBank accession No. J05242 (See also Frederick, et al., *J. Biol. Chem.*, 265(7):3793–802 (1990)) and the nucleotide sequences described in U.S. Pat. No. 5,879,921 can be used in obtaining nucleic acid encoding glucose oxidase.

In another example, the glucosone formation can be assessed by a combination of glucose 6-phosphate dehydrogenase and hexokinase. Any suitable glucose 6-phosphate dehydrogenase can be used. For example, glucose 6-phosphate dehydrogenase disclosed in the following patents and patent applications can be used: WO 03/042389, WO 01/98472, WO 93/06125, and U.S. Pat. Nos. 6,127,345, 6,069,297, 5,856,104, 5,308,770, 5,244,796, 5,229,286, 5,137,821 and 4,847,195. Any suitable hexokinase can be used. For example, hexokinase disclosed in the following patents and patent applications can be used: WO 02/20795, US2002/009779, WO 01/90378, WO 01/90325, WO 01/68694, WO 01/47968 and U.S. Pat. No 5,948,665.

If desirable, the protease can be inactivated before or current with the contact between the glycated peptide or glycated amino acid and the chimeric protein. The protease can be inactivated by any suitable methods. For example, the protease can be inactivated by a heat treatment or an inhibitor of the protease.

If desirable, interference of the assay can be countered. For example, ascorbate interference can be countered using a copper (II) compound, a cholic acid or a bathophenanthroline disulphonic acid or a mixture thereof Bilirubin interference can be countered using a ferrocyanide salt.

The present methods can be used for any suitable purpose. Preferably, the method used in the prognosis or diagnosis of a disease or disorder, e.g., diabetes.

In yet another aspect, the present invention is directed to a kit for assaying for a glycated protein in a sample, which kit comprises: a) a protease to generate glycated peptide or glycated amino acid from a glycated protein, if contained in a sample; b) a chimeric protein comprising, from N-terminus to C-terminus: i) a first peptidyl fragment comprising a bacterial leader sequence from about 5 to about 30 amino acid residues; and ii) a second peptidyl fragment comprising an amadoriase, to oxidize said glycated peptide or glycated amino acid; and c) means for assessing oxidation of said glycated peptide or glycated amino acid by said chimeric protein to determine the presence and/or amount of said glycated protein in said sample.

Any suitable means can be included in the present kits. For example, the means for assessing oxidation of said glycated peptide or glycated amino acid by said chimeric protein can comprise a peroxidase. Preferably, the chimeric protein and the peroxidase are formulated in a single composition.

D. Methods and Kits for Assaying for a Glycated Protein Using Proteinase K and an Amadoriase In yet another aspect, the present invention is directed to a method for assaying for a glycated protein in a sample, which method comprises: a) contacting a sample to be assayed with a proteinase K to generate a glycated peptide or a glycated amino acid from a glycated protein, if contained in said sample; b) contacting said generated glycated peptide or glycated amino acid with an amadoriase to oxidize said glycated peptide or glycated amino acid; and c) assessing oxidation of said glycated peptide or glycated amino acid by said amadoriase to determine the presence and/or amount of said glycated protein in said sample.

The present methods can be used to assay any suitable sample. Preferably, the sample is a blood sample, e.g., a plasma, serum, red blood cell or whole blood sample.

The present methods can be used to assay any suitable glycated proteins. Preferably, the glycated protein to be assayed is glycoalbumin or glycohemoglobin.

Any suitable amadoriase, including the ones described in the above Sections B and C, can be used in the present methods. For example, the amadoriase can comprise a chimeric protein, which chimeric protein comprises, from N-terminus to C-terminus: a) a first peptidyl fragment comprising a bacterial leader sequence from about 5 to about 30 amino acid residues; and b) a second peptidyl fragment comprising an amadoriase. Preferably, the chimeric protein comprises the amino acid sequence set forth in SEQ ID NO:5. Also preferably, the chimeric protein is encoded by the nucleotide sequence set forth in SEQ ID NO:6.

The oxidation of the glycated peptide or glycated amino acid can be assessed by any suitable methods. For example, the oxidation of the glycated peptide or glycated amino acid can be assessed by assessing consumption of the glycated peptide or glycated amino acid, $H_2O$ or $O_2$ in the oxidation reaction or the formation of the oxidized glucose (glucosone), $H_2O_2$ or the amino acid in the oxidation reaction.

The $O_2$ consumption can be assessed by any suitable methods. For example, the $O_2$ consumption can be assessed by an oxygen electrode.

The $H_2O_2$ formation can be assessed by any suitable methods. For example, the $H_2O_2$ formation can be assessed by a peroxidase. Any peroxidase, including the ones described in the above Sections C, can be used in the present methods. More preferably, a horseradish peroxidase is used. In another example, the $H_2O_2$ formation can be assessed by a peroxidase and Trinder reaction. The glycated peptide or glycated amino acid can be contacted with the chimeric protein and the peroxidase sequentially or simultaneously.

The glucosone formation can be assessed by any suitable methods. For example, the glucosone formation can be assessed by a glucose oxidase. Any suitable glucose oxidase, including the ones described in the above Sections C, can be used.

In another example, the glucosone formation can be assessed by a combination of glucose 6-phosphate dehydrogenase and hexokinase. Any suitable glucose 6-phosphate dehydrogenase, including the ones described in the above Sections C, can be used. Any suitable hexokinase, including the ones described in the above Sections C, can be used.

Any suitable proteinase K can be used in the present methods. For example, proteinase K disclosed in the following patents and patent applications can be used: WO 02/072634, WO 02/064760, WO 96/28556, and U.S. Pat. Nos. 6,451,574 and 5,344,770. Preferably, proteinase K from Tritirachium album is used (See e.g., Sigma-Aldrich Catalog No. 82452).

If desirable, the proteinase K can be inactivated before or concurrent with the contact between the glycated peptide or glycated amino acid and the amadoriase. For example, the proteinase K can be inactivated by a heat treatment or an inhibitor of the proteinase K.

If desirable, interference of the assay can be countered. For example, ascorbate interference can be countered using a copper (II) compound, a cholic acid or a bathophenanthroline disulphonic acid or a mixture thereof. Bilirubin interference can be countered using a ferrocyanide salt.

The present methods can be used for any suitable purpose. Preferably, the method used in the prognosis or diagnosis of a disease or disorder, e.g., diabetes.

In yet another aspect, the present invention is directed to a kit for assaying for a glycated protein in a sample, which kit comprises: a) a proteinase K to generate a glycated peptide or a glycated amino acid from a glycated protein, if contained in said sample; b) an amadoriase to oxidize said glycated peptide or glycated amino acid; and c) means for assessing oxidation of said glycated peptide or glycated amino acid by said amadoriase to determine the presence and/or amount of said glycated protein in said sample.

Any suitable means can be included in the present kits. For example, the means for assessing oxidation of said glycated peptide or glycated amino acid by said chimeric protein can comprise a peroxidase. Preferably, the chimeric protein and the peroxidase are formulated in a single composition.

Any suitable amadoriase, including the ones described in the above Sections B and C, can be used in the present kits. For example, the amadoriase can comprise a chimeric protein, which chimeric protein comprises, from N-terminus to C-terminus: a) a first peptidyl fragment comprising a bacterial leader sequence from about 5 to about 30 amino acid residues; and b) a second peptidyl fragment comprising an amadoriase. Preferably, the chimeric protein comprises the amino acid sequence set forth in SEQ ID NO:5. Also preferably, the chimeric protein is encoded by the nucleotide sequence set forth in SEQ ID NO:6.

EXAMPLES

Example 1

Glycated Serum Protein Enzymatic Assay Kit

Intended Use. The exemplary assay kit is for determination of glycated serum proteins (fructosamine) in human serum. Fructosamine is formed due to a non-enzymatic Maillard reaction between glucose and amino acid residues of proteins. In diabetic patients, elevated blood glucose levels correlate with increased fructosamine formation. Fructosamine is a medium term indicator of diabetic control (2–3 weeks).

Assay Principle. The exemplary enzymatic assay for glycated serum proteins (GSP) uses Proteinase K to digest GSP into low molecular weight glycated protein fragments (GPF), and uses Diazyme's specific fructosaminase™, a microorganism originated amadoriase to catalyze the oxidative degradation of Amadori product GPF to yield PF or amino acids, glucosone and $H_2O_2$. The $H_2O_2$ released is measured by a colorimetric Trinder end-point reaction. The absorbance at 550 nm is proportional to the concentration of glycated serum proteins (GSP).

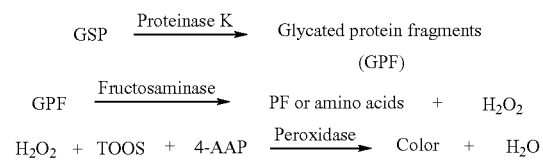

TABLE 4

| Reagent Table | |
| --- | --- |
| Reagent 1 (R1) Lyophilized 2 × 20 mL | Proteinase K, buffer |
| Reagent 2 (R2) Lyophilized 2 × 5 mL | Fructosaminase ™, HRP, buffer |

Test Samples. Use fresh patient serum or EDTA treated plasma samples. Plasma should be separated from cells immediately after collection. Samples can be stored at 4° C. for 2 weeks or up to 4 weeks when frozen.

Reconstitution. One vial of Reagents 1 is reconstituted with 20 mL of distilled water. Mix gently by inversion and then allow to stand for a minimum of 10 min at room temperature before use. The reconstituted RI is stable for 4 weeks at 4° C. One vial of Reagent 2 is reconstituted with 5 mL of distilled water. Mix gently by inversion and then allow to stand at room temperature for minimum of 10 min before use. The reconstituted R2 is stable for 6 weeks at 4° C.

Assay Procedure
1. Pre-warm reconstituted R1 and R2 at room temperature.
2. Instrumental parameters.
   Wavelength: 550 nm; reference 700 nm
   Cuvette: 1 cm light path
   Temperature: 37° C.
3. Add 200 μL of the reconstituted R1 and 50 μL of sample or calibrator into cuvette. Mix and incubate for 5 min. Read absorbance at 550 nm as $A_1$.
4. Add 50 μL of the reconstituted R2, mix and incubate for further 5 min and then read the absorbance at 550 nm as $A_2$.
5. Reagent blank absorbance is read by using 50 μL of $H_2O$ instead of sample or calibrator.

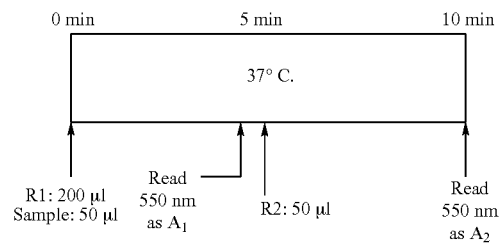

Calculation $$\Delta A = A_2 - A_1$$

Concentration of Glycated Serum Proteins (Fructosamine) in Sample:

$$\text{Fructosamine (μmole/L)} = \Delta A\text{sample} - \Delta A\text{blank} \times \text{Conc. of calibrator}$$

Normal values. Adults (20–60 years) have a normal range of 122–285 μmol/L. Each laboratory should establish an expected range with a set of standards.

Linearity and Sensitivity. The assay is linear up to 1200 μmol/L and is sensitive at 30 μmol/L. The Diazyme Glycated Serum Protein (fructosamine) assay is precise with a mean inter-assay CV of <3% and mean intra assay CV of <2%. Assay data showed excellent correlation with the alternative fructosamine measurement method with $r^2 = 0.99$.

Interferences. The following analyte concentrations were not found to affect the assay:

Ascorbic acid (4 mg/dL)
Bilirubin (2 mg/dL).
Glucose (1200 mg/dL
Hemoglobin (100 mg/dL)
Triglycerides (250 mg/dL)
Uric acid (15 mg/dL)

Calibration. Fructosamine Calibrator (Cat. No. DZ112A-S) is required for calibration.

Quality Control. Fructosamine Controls (low and high) (Cat. No. DZ112A-C1 and DZ112A-C3) are recommended to use as control sera. One control (low or high) should be tested after every 30 samples. Values should fall within a specific range. If these values fall outside the range and repetition excludes error, the following steps should be taken:

1. Check instrument settings and light source;
2. Check reaction temperature;
3. Check expiry date of kit and contents; and
4. Check the quality of the water used for reagents reconstitution.

REFERENCES

Armbuster D A, Fructosamine: Structure, Analysis and Clinical Usefulness. *Clin. Chem.* 1987; 33 (12): 2153–2163.

Kouzuma, T. et al. An enzymatic method for the measurement of glycated albumin in biological samples. *Clin. Chimi. Acta* 2002; 324: 61–71.

Example 2

Glycated Serum Protein Assay Precision and Linearity
Method Comparison

Determined by running 2 replicates of a set of random samples using both Diazyme GSP kit and Randox Fructosamine kit in one run. The analytical performance characteristics determined by Diazyme GSP kit were comparable to those observed with Randox Fructosamine kit when assays were performed under the conditions as described in the Example 1 (See also FIG. 1).

Assay Linearity

Figure 2:
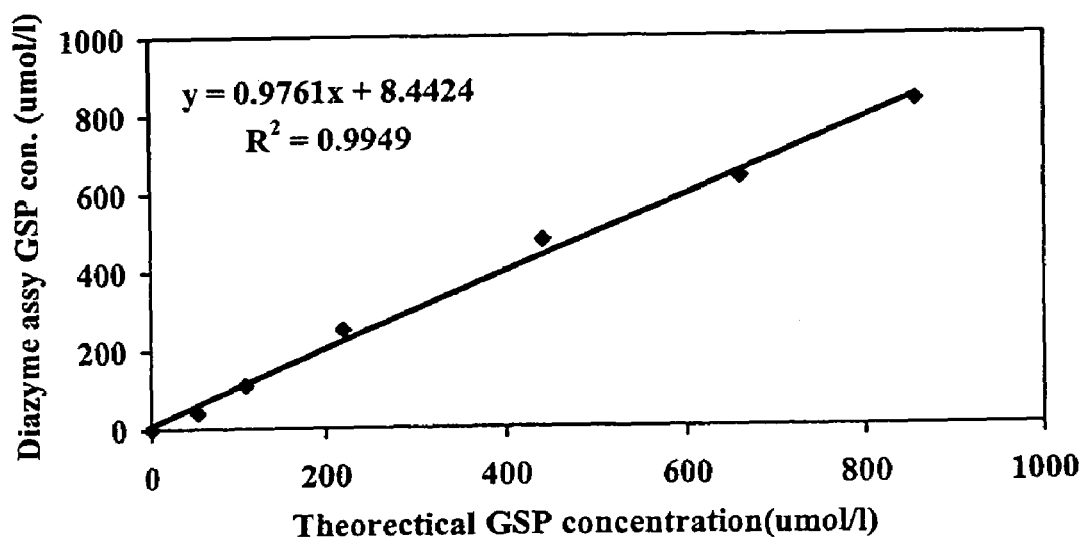
FIG. 2 illustrates assay linearity of an exemplary method for assaying for a glycated protein in a sample.

Determined by running 2 replicates of a set of series diluted serum samples in one run. The assay is linear from 40–856 umole/L (See FIG. 2).

Interference

Determined by running 3 replicates each of a control sample in the absence and presence of various potential interference substances at indicated concentrations (See the following Table 5).

TABLE 5

| Interference analysis | | |
|---|---|---|
| Interfering substances | Interfering substance concentration | % Interference |
| Ascorbic Acid | 4 mg/dL | −0.3 |
| Bilirubin | 2 mg/dL | −0.6 |
| Glucose | 1200 mg/dL | −0.6 |
| Hemoglobin | 100 mg/dL | −4.4 |
| Triglycerol | 250 mg/dL | 1.2 |
| Uric Acid | 15 mg/dL | 5.3 |

Example 3

Assay for Glycated Hemoglobin HbAlc

A. Glycated Valine Measurement:

1. Mix 10 ul 170 mM Glycated Valine (G-Valine) (This value was assumed all valine was converted_to G-Valine in the cooking procedure.) with 300 ul R1 (80 mMCHES, 30 mmMOPS, 0.9% BRIJ). This mixture serves as sample stock solution (GVR1).

Figure 3:
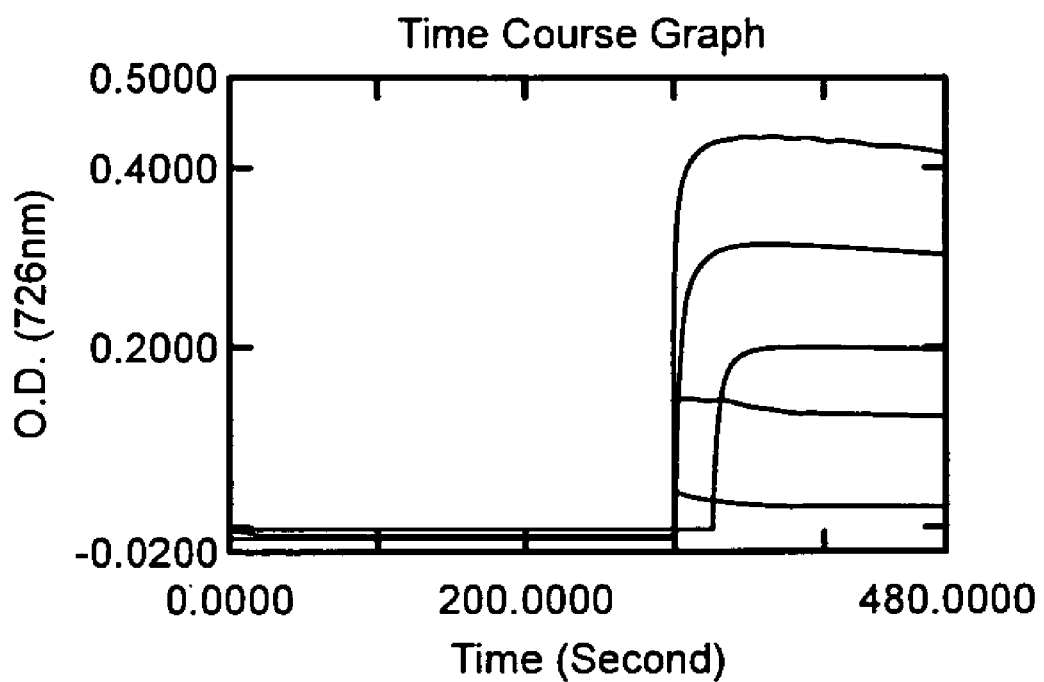
FIGS. 3 and 4 show the dose-dependent reaction with fructosyl-valine.
Figure 4:
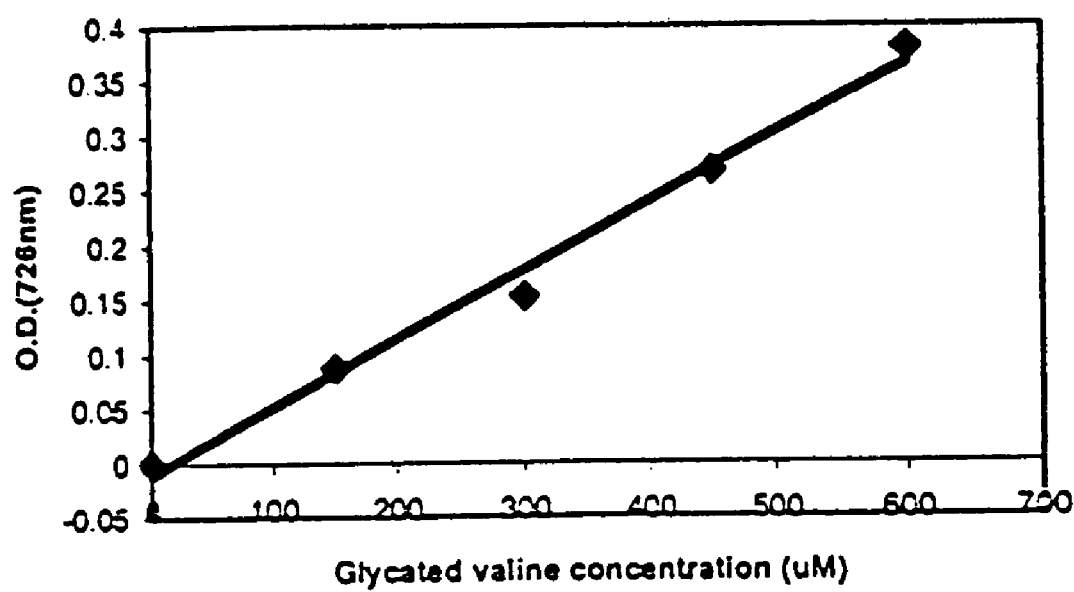

2. Set spectrometer wavelength at 726 nm, temperature at 37° C. Pipette 150 ul_R2 (30 mMMES, 1 mMCaCl2, 2 mMWST-3, 1570 U/ml Proteinase K) to a cuvette, add 0 ul, 2.5 ul, 5 ul, 10 ul, 15 ul, 20 ul above GVR1 respectively for dose response, make up the sample volume to 20 ul with $H_2O$ in R1, incubate for 5 min, get the first O.D. reading, then add 30 ul R3 (0.08 mMDA-64, 240 mMTris, 180 U/ml HRP, 20 U/ml FAOD), incubate for 3 min, get the second O.D. reading. Calculate the O.D. difference between these two readings, using 20 ul $H_2O$ in R1 as control. FIGS. 3 and 4 show the dose-dependent reaction with fructosyl-valine.

B. Glycated Hemoglobin Measurement:

1. Mix 10 ul high level Glycated Hemoglobin (G-hg (HHg)), 10 ul mid level G-hg(MHg), 10 ul normal_level G-hg (NMHg) respectively with 300 ul R1.

2. Set spectrometer wavelength at 570 nm, temperature at 37° C. Pipette 150 ul_R2 to cuvette, add 20 ul above Hg in R1 as sample, read the O.D. after 4 min incubation, using $H_2O$ in R1 as control. This O.D. reading gives the relative Hg concentration.

Figure 5:
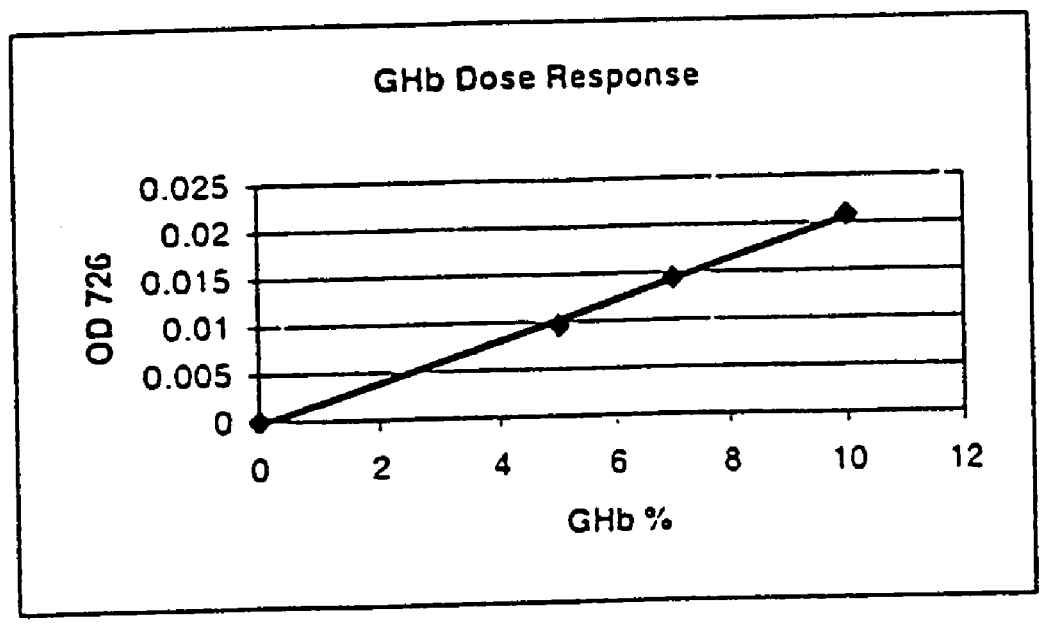
FIG. 5 shows the dose-dependent signal with patient hemoglobin digested with a proteinase (5 min. digestion).

3. Change the spectrometer wavelength to 726 nm, get the first O.D._reading, add 30 ul R3, incubate for 5 min, get the second O.D. reading. Calculate the O.D. difference between these two readings. _Normalize these O.D. differences of the three samples with their Hg concentrations. FIG. 5 shows the dose-dependent signal with patient hemoglobin digested with a proteinase (5 min. digestion).

The above examples are included for illustrative purposes only and are not intended to limit the scope of the invention. Many variations to those described above are possible. Since modifications and variations to the examples described above will be apparent to those of skill in this art, it is intended that this invention be limited only by the scope of the appended claims.

What is claimed is:

1. An isolated chimeric protein having enzymatic activity of an amadoriase, which chimeric protein comprises, from N-terminus to C-terminus:
   a) a first peptidyl fragment comprising a bacterial leader sequence comprising the amino acid sequence set forth in SEQ ID NO:1;
   b) a second peptidyl fragment comprising an amadoriase comprising the amino acid sequence set forth in SEQ ID NO:3; and
   c) a third peptidyl fragment comprising a second bacterial leader sequence comprising the amino acid sequence set forth in SEQ ID NO:4.

2. The isolated chimeric protein of claim 1, wherein the first and second peptidyl fragments are linked via a cleavable linkage.

3. The isolated chimeric protein of claim 1, which further comprises, at its C-terminus, a fourth peptidyl fragment comprising a peptide tag.

4. The isolated chimeric protein of claim 3, wherein the peptide tag is selected from the group consisting of FLAG, HA, HA1, c-Myc, 6-His, AU1, EE, T7, 4A6, ε, B, gE and Tyl tag.

5. The isolated chimeric protein of claim 1, which comprises the amino acid sequence set forth in SEQ ID NO:5

(MGGSGDDDDLALAVTKSSSLLIVGAGTWGTSTALHLARRGYTNVTVLD

PYPVPSAISAGNDVNKVISSGQYSNNKDEIEVNEILAEEAFNGWKNDPLF

KPYYHDTGLLMSACSQEGLDRLGVRVRPGEDPNLVELTRPEQFRKLAPEG

VLQGDFPGWKGYFARSGAGWAHARNALVAAAREAQRMGVKFVTGTPQG

RVVTLIFENNDVKGAVTGDGKIWRAERTFLCAGASAGQFLDFKNQLRPT

AWTLVHIALKPEERALYKNIPVIFNIERGFFFEPDEERGEIKICDEHPGY

TNMVQSADGTMMSIPFEKTQIPKEAETRVRALLKETMPQLADRPFSFARI

CWCADTANREFLIDRHPQYHSLVLGCGASGRGFKYLPSIGNLIVDAMEGK

VPQKIHELIKWNPDIAANRNWRDTLGRFGGPNRVMDFHDVKEWTNVQYRD

ISKLKGELEGLPIPNPLLRTGHHHHHH).

6. A chimeric protein produced by growing a recombinant cell containing a nucleic acid comprising a nucleotide sequence encoding the chimeric protein of claim 1 such that the encoded chimeric protein is expressed by the cell, and recovering the expressed chimeric protein.

7. A method for assaying for a glycated protein in a sample, which method comprises:
   a) contacting a sample to be assayed with a protease to generate a glycated peptide or a glycated amino acid from a glycated protein, if contained in said sample;
   b) contacting said generated glycated peptide or glycated amino acid with a chimeric protein of claim 1 to oxidize said glycated peptide or glycated amino acid; and
   c) assessing oxidation of said glycated peptide or glycated amino acid by said chimeric protein to determine the presence and/or amount of said glycated protein in said sample.

8. The method of claim 7, wherein the sample is a blood sample.

9. The method of claim 8, wherein the blood sample is a plasma, serum, red blood cell or whole blood sample.

10. The method of claim 7, wherein the glycated protein to be assayed is glycoalbumin or glycohemoglobin.

11. The method of claim 7, wherein the protease is an endo-type protease or an exo-type protease.

12. The method of claim 11, wherein the endo-type protease is selected from the group consisting of trypsin, α-chymotrypsin, subtilisin, proteinase K, papain, cathepsin B, pepsin, thermolysin, protease XVII, protease XXI, lysylendopeptidase, proleather and bromelain F.

13. The method of claim 11, wherein the exo-type protease is an aminopeptidase or a carboxypeptidase.

14. The method of claim 7, wherein the protease is selected from the group consisting of proteinase K, pronase E, ananine, thermolysin, subtilisin and cow pancreas proteases.

15. The method of claim 7, wherein the protease generates a glycated peptide from about 2 to about 30 amino acid residues.

16. The method of claim 7, wherein the protease generates glycated glycine, glycated valine or glycated lysine residue or a glycated peptide comprising glycated glycine, glycated valine or glycated lysine residue.

17. The method of claim 7, wherein the chimeric protein comprises the amino acid sequence set forth in SEQ ID NO:5.

18. The method of claim 7, wherein the chimeric protein is encoded by the nucleotide sequence set forth in SEQ ID NO:6.

19. The method of claim 7, wherein the oxidation of the glycated peptide or glycated amino acid is assessed by assessing consumption of the glycated peptide or glycated amino acid, or $O_2$ in the oxidation reaction or the formation of the oxidized glucose (glucosone), $H_2O_2$ or the amino acid in the oxidation reaction.

20. The method of claim 19, wherein the $O_2$ consumption is assessed by an oxygen electrode.

21. The method of claim 19, wherein the $H_2$ formation is assessed by a peroxidase.

22. The method of claim 21, wherein the peroxidase is horseradish peroxidase.

23. The method of claim 21, wherein the $H_2O_2$ formation is assessed by a peroxidase and Trinder reaction.

24. The method of claim 21, wherein the glycated peptide or glycated amino acid is contacted with the chimeric protein and the peroxidase sequentially or simultaneously.

25. The method of claim 19, wherein the glucosone formation is assessed by a glucose oxidase.

26. The method of claim 19, wherein the glucosone formation is assessed by a combination of glucose 6-phosphate dehydrogenase and hexokinase.

27. The method of claim 7, wherein the protease is inactivated before or current with the contact between the glycated peptide or glycated amino acid and the chimeric protein.

28. The method of claim 27, wherein the protease is inactivated by an inhibitor of the protease, or by a heat treatment if the protease is inactivated before the contact between the glycated peptide or glycated amino acid and the chimeric protein.

29. The method of claim 7, wherein ascorbate interference is countered using a copper (II) compound, a cholic acid or a bathophenanthroline disulphonic acid or a mixture thereof.

30. The method of claim 7, wherein bilirubin interference is countered using a ferrocyanide salt.

31. The method of claim 7, which is used in the prognosis or diagnosis of a disease or disorder.

32. The method of claim 31, wherein the disease or disorder is diabetes.

33. A kit for assaying for a glycated protein in a sample, which kit comprises:
   a) a protease to generate glycated peptide or glycated amino acid from a glycated protein, if contained in a sample;
   b) a chimeric protein of claim 1 to oxidize said glycated peptide or glycated amino acid; and
   c) means for assessing oxidation of said glycated peptide or glycated amino acid by said chimeric protein to determine the presence and/or amount of said glycated protein in said sample.

34. The kit of claim 33, wherein the means for assessing oxidation of said glycated peptide or glycated amino acid by said chimeric protein comprises peroxidase.

35. The kit of claim 34, wherein the chimeric protein and the peroxidase are formulated in a single composition.

* * * * *

SEQUENCE LISTING

<160> NUMBER OF SEQ ID NOS: 23

<210> SEQ ID NO 1
<211> LENGTH: 12
<212> TYPE: PRT
<213> ORGANISM: Artificial Sequence
<220> FEATURE:
<223> OTHER INFORMATION: 40%-100% identity to leader sequence

<400> SEQUENCE: 1

Met Gly Gly Ser Gly Asp Asp Asp Asp Leu Ala Leu
 1               5                  10

<210> SEQ ID NO 2
<211> LENGTH: 6
<212> TYPE: PRT
<213> ORGANISM: Artificial Sequence
<220> FEATURE:
<223> OTHER INFORMATION: FAD cofactor-binding consensus sequence
<220> FEATURE:
<221> NAME/KEY: VARIANT
<222> LOCATION: 2, 4, 5
<223> OTHER INFORMATION: Xaa = Any Amino Acid

<400> SEQUENCE: 2

Gly Xaa Gly Xaa Xaa Gly
 1               5

<210> SEQ ID NO 3
<211> LENGTH: 437
<212> TYPE: PRT
<213> ORGANISM: Artificial Sequence
<220> FEATURE:
<223> OTHER INFORMATION: 40%-100% identity to the amadoriase

<400> SEQUENCE: 3

Ala Val Thr Lys Ser Ser Ser Leu Leu Ile Val Gly Ala Gly Thr Trp
 1               5                  10                  15

Gly Thr Ser Thr Ala Leu His Leu Ala Arg Arg Gly Tyr Thr Asn Val
                20                  25                  30

Thr Val Leu Asp Pro Tyr Pro Val Pro Ser Ala Ile Ser Ala Gly Asn
            35                  40                  45

Asp Val Asn Lys Val Ile Ser Ser Gly Gln Tyr Ser Asn Asn Lys Asp
        50                  55                  60

Glu Ile Glu Val Asn Glu Ile Leu Ala Glu Glu Ala Phe Asn Gly Trp
 65                  70                  75                  80

Lys Asn Asp Pro Leu Phe Lys Pro Tyr Tyr His Asp Thr Gly Leu Leu
                85                  90                  95

Met Ser Ala Cys Ser Gln Glu Gly Leu Asp Arg Leu Gly Val Arg Val
            100                 105                 110

Arg Pro Gly Glu Asp Pro Asn Leu Val Glu Leu Thr Arg Pro Glu Gln
        115                 120                 125

Phe Arg Lys Leu Ala Pro Glu Gly Val Leu Gln Gly Asp Phe Pro Gly
    130                 135                 140

Trp Lys Gly Tyr Phe Ala Arg Ser Gly Ala Gly Trp Ala His Ala Arg
145                 150                 155                 160

Asn Ala Leu Val Ala Ala Ala Arg Glu Ala Gln Arg Met Gly Val Lys
                165                 170                 175

Phe Val Thr Gly Thr Pro Gln Gly Arg Val Val Thr Leu Ile Phe Glu
            180                 185                 190

```
Asn Asn Asp Val Lys Gly Ala Val Thr Gly Asp Gly Lys Ile Trp Arg
        195                 200                 205
Ala Glu Arg Thr Phe Leu Cys Ala Gly Ala Ser Ala Gly Gln Phe Leu
        210                 215                 220
Asp Phe Lys Asn Gln Leu Arg Pro Thr Ala Trp Thr Leu Val His Ile
225                 230                 235                 240
Ala Leu Lys Pro Glu Glu Arg Ala Leu Tyr Lys Asn Ile Pro Val Ile
                245                 250                 255
Phe Asn Ile Glu Arg Gly Phe Phe Glu Pro Asp Glu Arg Gly
                260                 265                 270
Glu Ile Lys Ile Cys Asp Glu His Pro Gly Tyr Thr Asn Met Val Gln
        275                 280                 285
Ser Ala Asp Gly Thr Met Met Ser Ile Pro Phe Glu Lys Thr Gln Ile
        290                 295                 300
Pro Lys Glu Ala Glu Thr Arg Val Arg Ala Leu Leu Lys Glu Thr Met
305                 310                 315                 320
Pro Gln Leu Ala Asp Arg Pro Phe Ser Phe Ala Arg Ile Cys Trp Cys
                325                 330                 335
Ala Asp Thr Ala Asn Arg Glu Phe Leu Ile Asp Arg His Pro Gln Tyr
                340                 345                 350
His Ser Leu Val Leu Gly Cys Gly Ala Ser Gly Arg Gly Phe Lys Tyr
        355                 360                 365
Leu Pro Ser Ile Gly Asn Leu Ile Val Asp Ala Met Glu Gly Lys Val
        370                 375                 380
Pro Gln Lys Ile His Glu Leu Ile Lys Trp Asn Pro Asp Ile Ala Ala
385                 390                 395                 400
Asn Arg Asn Trp Arg Asp Thr Leu Gly Arg Phe Gly Pro Asn Arg
                405                 410                 415
Val Met Asp Phe His Asp Val Lys Glu Trp Thr Asn Val Gln Tyr Arg
                420                 425                 430
Asp Ile Ser Lys Leu
        435

<210> SEQ ID NO 4
<211> LENGTH: 17
<212> TYPE: PRT
<213> ORGANISM: Artificial Sequence
<220> FEATURE:
<223> OTHER INFORMATION: 40%-100% identity of the second bacterial
      leader sequence

<400> SEQUENCE: 4

Lys Gly Glu Leu Glu Gly Leu Pro Ile Pro Asn Pro Leu Leu Arg Thr
1               5                   10                  15

Gly

<210> SEQ ID NO 5
<211> LENGTH: 472
<212> TYPE: PRT
<213> ORGANISM: Artificial Sequence
<220> FEATURE:
<223> OTHER INFORMATION: chimeric protein

<400> SEQUENCE: 5

Met Gly Gly Ser Gly Asp Asp Asp Leu Ala Leu Ala Val Thr Lys
1               5                   10                  15

Ser Ser Ser Leu Leu Ile Val Gly Ala Gly Thr Trp Gly Thr Ser Thr
```

-continued

```
                    20                  25                  30
Ala Leu His Leu Ala Arg Arg Gly Tyr Thr Asn Val Thr Val Leu Asp
             35                  40                  45
Pro Tyr Pro Val Pro Ser Ala Ile Ser Ala Gly Asn Asp Val Asn Lys
         50                  55                  60
Val Ile Ser Ser Gly Gln Tyr Ser Asn Asn Lys Asp Glu Ile Glu Val
 65                  70                  75                  80
Asn Glu Ile Leu Ala Glu Glu Ala Phe Asn Gly Trp Lys Asn Asp Pro
                 85                  90                  95
Leu Phe Lys Pro Tyr Tyr His Asp Thr Gly Leu Leu Met Ser Ala Cys
             100                 105                 110
Ser Gln Glu Gly Leu Asp Arg Leu Gly Val Arg Val Arg Pro Gly Glu
         115                 120                 125
Asp Pro Asn Leu Val Glu Leu Thr Arg Pro Glu Gln Phe Arg Lys Leu
 130                 135                 140
Ala Pro Glu Gly Val Leu Gln Gly Asp Phe Pro Gly Trp Lys Gly Tyr
145                 150                 155                 160
Phe Ala Arg Ser Gly Ala Gly Trp Ala His Ala Arg Asn Ala Leu Val
                 165                 170                 175
Ala Ala Ala Arg Glu Ala Gln Arg Met Gly Val Lys Phe Val Thr Gly
             180                 185                 190
Thr Pro Gln Gly Arg Val Val Thr Leu Ile Phe Glu Asn Asn Asp Val
         195                 200                 205
Lys Gly Ala Val Thr Gly Asp Gly Lys Ile Trp Arg Ala Glu Arg Thr
 210                 215                 220
Phe Leu Cys Ala Gly Ala Ser Ala Gly Gln Phe Leu Asp Phe Lys Asn
225                 230                 235                 240
Gln Leu Arg Pro Thr Ala Trp Thr Leu Val His Ile Ala Leu Lys Pro
                 245                 250                 255
Glu Glu Arg Ala Leu Tyr Lys Asn Ile Pro Val Ile Phe Asn Ile Glu
             260                 265                 270
Arg Gly Phe Phe Phe Glu Pro Asp Glu Glu Arg Gly Glu Ile Lys Ile
         275                 280                 285
Cys Asp Glu His Pro Gly Tyr Thr Asn Met Val Gln Ser Ala Asp Gly
 290                 295                 300
Thr Met Met Ser Ile Pro Phe Glu Lys Thr Gln Ile Pro Lys Glu Ala
305                 310                 315                 320
Glu Thr Arg Val Arg Ala Leu Leu Lys Glu Thr Met Pro Gln Leu Ala
                 325                 330                 335
Asp Arg Pro Phe Ser Phe Ala Arg Ile Cys Trp Cys Ala Asp Thr Ala
             340                 345                 350
Asn Arg Glu Phe Leu Ile Asp Arg His Pro Gln Tyr His Ser Leu Val
         355                 360                 365
Leu Gly Cys Gly Ala Ser Gly Arg Gly Phe Lys Tyr Leu Pro Ser Ile
 370                 375                 380
Gly Asn Leu Ile Val Asp Ala Met Glu Gly Lys Val Pro Gln Lys Ile
385                 390                 395                 400
His Glu Leu Ile Lys Trp Asn Pro Asp Ile Ala Ala Asn Arg Asn Trp
                 405                 410                 415
Arg Asp Thr Leu Gly Arg Phe Gly Gly Pro Asn Arg Val Met Asp Phe
             420                 425                 430
His Asp Val Lys Glu Trp Thr Asn Val Gln Tyr Arg Asp Ile Ser Lys
         435                 440                 445
```

Leu Lys Gly Glu Leu Glu Gly Leu Pro Ile Pro Asn Pro Leu Leu Arg
     450                 455                 460

Thr Gly His His His His His
465                 470

<210> SEQ ID NO 6
<211> LENGTH: 1419
<212> TYPE: DNA
<213> ORGANISM: Artificial Sequence
<220> FEATURE:
<223> OTHER INFORMATION: nucleotide sequence encoding a chimeric protein

<400> SEQUENCE: 6

| | | | | | |
|---|---|---|---|---|---|
| atgggaggtt | cgggtgacga | tgatgacctg | gctctcgccg | tcactaagtc | atcatctctc | 60 |
| ctgatcgttg | gtgccgggac | ttggggcacc | tcaacggctc | tgcacctcgc | gcgccgcgga | 120 |
| tataccaacg | ttaccgtgct | ggaccccctat | cctgtcccta | gcgccatctc | cgccggaaac | 180 |
| gacgtgaaca | agtcattag | cagtggccaa | tattcgaata | caaagacga | aatcgaagtg | 240 |
| aatgagatct | tggcggaaga | ggcgtttaac | ggttggaaga | cgacccgct | tttcaaaccg | 300 |
| tattatcatg | atacgggcct | gctgatgtct | gcttgctcgc | aggagggcct | ggatcgcctg | 360 |
| ggcgtccggg | tacgtccggg | cgaggatcct | aatctggtgg | aacttacccg | cccggagcaa | 420 |
| tttcgtaaac | tggccccgga | aggcgtgttg | caaggtgatt | ttccggggttg | gaaagggtac | 480 |
| tttgcgcgtt | ccggcgctgg | ctgggcacat | gcaaggaatg | ccttagtggc | agcagcacgc | 540 |
| gaagcacagc | gcatgggtgt | aaaatttgtt | actggcaccc | cgcagggtcg | tgtagtcacg | 600 |
| ttaatctttg | aaaataacga | tgtaaaaggt | gccgttacgg | gcgatggcaa | aatttggaga | 660 |
| gcggaacgta | cattcctgtg | tgctgggggct | agcgcgggtc | agttcctaga | tttcaagaat | 720 |
| caacttcgac | caaccgcttg | gaccctggta | cacattgcgt | taaaaccgga | gaacgtgcg | 780 |
| ttgtacaaaa | atataccggt | tatctttaac | atcgaacggg | ggttttttctt | tgaacccgat | 840 |
| gaggagcgcg | gtgagattaa | aatatgcgat | gaacacccgg | gctacacaaa | tatggtccag | 900 |
| agtgcagacg | gcacgatgat | gagcattccg | ttcgaaaaaa | cccagattcc | aaaagaagcc | 960 |
| gaaacgcgcg | ttcgggccct | gctgaaagag | acaatgcccc | agctggcaga | ccgtccattc | 1020 |
| agcttcgcac | gcatttgctg | gtgtgccgat | accgcgaatc | gcgaattcct | gatagatcga | 1080 |
| catccgcagt | accacagtct | tgtgttgggc | tgtggtgcga | gcggaagagg | gtttaaatat | 1140 |
| ctgccttcta | ttgggaatct | cattgttgac | gcgatggaag | gtaaagtgcc | gcaaaaaatt | 1200 |
| cacgaattaa | tcaagtggaa | cccggacatt | gcggcgaacc | gtaactggcg | tgatactctg | 1260 |
| gggcgttttg | gcggtccaaa | tcgtgtgatg | gattttcatg | atgtgaagga | atggaccaat | 1320 |
| gttcagtatc | gtgatatttc | caagctgaaa | ggagagttgg | aaggtaagcc | aatccctaac | 1380 |
| ccgttactgc | gcacaggcca | tcaccatcat | catcattaa | | | 1419 |

<210> SEQ ID NO 7
<211> LENGTH: 39
<212> TYPE: PRT
<213> ORGANISM: Artificial Sequence
<220> FEATURE:
<223> OTHER INFORMATION: sequence homology between the N-terminal
      sequence of Amadoriases Ia
<220> FEATURE:
<221> NAME/KEY: VARIANT
<222> LOCATION: 12
<223> OTHER INFORMATION: Xaa = C or T

<400> SEQUENCE: 7

```
Ala Pro Ser Ile Leu Ser Thr Glu Ser Ile Xaa Val Ile Gly Ala
1               5                   10                  15

Gly Thr Trp Gly Gly Gly Gly Gly Gly Gly Gly Gly Gly Gly
            20                  25                  30

Gly Gly Gly Gly Gly Gly Gly
            35
```

<210> SEQ ID NO 8
<211> LENGTH: 39
<212> TYPE: PRT
<213> ORGANISM: Artificial Sequence
<220> FEATURE:
<223> OTHER INFORMATION: Sequence homology between the N-terminal
      sequence of Amadoriase Ib

<400> SEQUENCE: 8

```
Ala Pro Ser Ile Leu Ser Thr Glu Ser Ile Ile Val Ile Gly Ala
1               5                   10                  15

Gly Thr Trp Gly Gly Gly Gly Gly Gly Gly Gly Gly Gly Gly
            20                  25                  30

Gly Gly Gly Gly Gly Gly Gly
            35
```

<210> SEQ ID NO 9
<211> LENGTH: 39
<212> TYPE: PRT
<213> ORGANISM: Artificial Sequence
<220> FEATURE:
<223> OTHER INFORMATION: Sequence homology between the N-terminal
      sequence of Amadoriase Ic

<400> SEQUENCE: 9

```
Ser Thr Glu Ser Ser Ile Ile Val Ile Gly Ala Gly Thr Trp Gly Cys
1               5                   10                  15

Ser Thr Ala Leu Leu Leu Leu Leu Leu Leu Leu Leu Leu Leu
            20                  25                  30

Leu Leu Leu Leu Leu Leu Leu
            35
```

<210> SEQ ID NO 10
<211> LENGTH: 39
<212> TYPE: PRT
<213> ORGANISM: Artificial Sequence
<220> FEATURE:
<223> OTHER INFORMATION: Sequence homology between the N-terminal
      sequence of Amadoriase II

<400> SEQUENCE: 10

```
Ala Val Thr Lys Ser Ser Ser Leu Leu Ile Val Gly Ala Gly Thr Trp
1               5                   10                  15

Gly Thr Ser Thr Thr Thr Thr Thr Thr Thr Thr Thr Thr Thr Thr
            20                  25                  30

Thr Thr Thr Thr Thr Thr Thr
            35
```

<210> SEQ ID NO 11
<211> LENGTH: 7
<212> TYPE: PRT
<213> ORGANISM: Artificial Sequence
<220> FEATURE:
<223> OTHER INFORMATION: exemplary epitope tag

<400> SEQUENCE: 11

```
Asp Tyr Lys Asp Asp Asp Lys
 1               5
```

<210> SEQ ID NO 12
<211> LENGTH: 9
<212> TYPE: PRT
<213> ORGANISM: Artificial Sequence
<220> FEATURE:
<223> OTHER INFORMATION: exemplary epitope tag

<400> SEQUENCE: 12

```
Tyr Pro Tyr Asp Val Pro Asp Tyr Ala
 1               5
```

<210> SEQ ID NO 13
<211> LENGTH: 11
<212> TYPE: PRT
<213> ORGANISM: Artificial Sequence
<220> FEATURE:
<223> OTHER INFORMATION: exemplary epitope tag

<400> SEQUENCE: 13

```
Cys Gln Asp Leu Pro Gly Asn Asp Asn Ser Thr
 1               5                   10
```

<210> SEQ ID NO 14
<211> LENGTH: 10
<212> TYPE: PRT
<213> ORGANISM: Artificial Sequence
<220> FEATURE:
<223> OTHER INFORMATION: exemplary epitope tag

<400> SEQUENCE: 14

```
Glu Gln Lys Leu Ile Ser Glu Glu Asp Leu
 1               5                   10
```

<210> SEQ ID NO 15
<211> LENGTH: 6
<212> TYPE: PRT
<213> ORGANISM: Artificial Sequence
<220> FEATURE:
<223> OTHER INFORMATION: exemplary epitope tag

<400> SEQUENCE: 15

```
His His His His His His
 1               5
```

<210> SEQ ID NO 16
<211> LENGTH: 6
<212> TYPE: PRT
<213> ORGANISM: Artificial Sequence
<220> FEATURE:
<223> OTHER INFORMATION: exemplary epitope tag

<400> SEQUENCE: 16

```
Asp Thr Tyr Arg Tyr Ile
 1               5
```

<210> SEQ ID NO 17
<211> LENGTH: 6
<212> TYPE: PRT
<213> ORGANISM: Artificial Sequence
<220> FEATURE:
<223> OTHER INFORMATION: exemplary epitope tag

<400> SEQUENCE: 17

```
Glu Tyr Met Pro Met Glu
1               5

<210> SEQ ID NO 18
<211> LENGTH: 11
<212> TYPE: PRT
<213> ORGANISM: Artificial Sequence
<220> FEATURE:
<223> OTHER INFORMATION: exemplary epitope tag

<400> SEQUENCE: 18

Ala Ser Met Thr Gly Gly Gln Gln Met Gly Arg
1               5                   10

<210> SEQ ID NO 19
<211> LENGTH: 10
<212> TYPE: PRT
<213> ORGANISM: Artificial Sequence
<220> FEATURE:
<223> OTHER INFORMATION: exemplary epitope tag

<400> SEQUENCE: 19

Ser Phe Pro Gln Phe Lys Pro Gln Glu Ile
1               5                   10

<210> SEQ ID NO 20
<211> LENGTH: 12
<212> TYPE: PRT
<213> ORGANISM: Artificial Sequence
<220> FEATURE:
<223> OTHER INFORMATION: exemplary epitope tag

<400> SEQUENCE: 20

Lys Gly Phe Ser Tyr Phe Gly Glu Asp Leu Met Pro
1               5                   10

<210> SEQ ID NO 21
<211> LENGTH: 6
<212> TYPE: PRT
<213> ORGANISM: Artificial Sequence
<220> FEATURE:
<223> OTHER INFORMATION: exemplary epitope tag

<400> SEQUENCE: 21

Gln Tyr Pro Ala Leu Thr
1               5

<210> SEQ ID NO 22
<211> LENGTH: 11
<212> TYPE: PRT
<213> ORGANISM: Artificial Sequence
<220> FEATURE:
<223> OTHER INFORMATION: exemplary epitope tag

<400> SEQUENCE: 22

Gln Arg Gln Tyr Gly Asp Val Phe Lys Gly Asp
1               5                   10

<210> SEQ ID NO 23
<211> LENGTH: 10
<212> TYPE: PRT
<213> ORGANISM: Artificial Sequence
<220> FEATURE:
<223> OTHER INFORMATION: exemplary epitope tag
```

<400> SEQUENCE: 23

Glu Val His Thr Asn Gln Asp Pro Leu Asp
1               5                   10